(12) United States Patent
Merckle et al.

(10) Patent No.: US 10,456,507 B2
(45) Date of Patent: Oct. 29, 2019

(54) TISSUE FUSION AGENT

(71) Applicant: Aesculap AG, Tuttlingen (DE)

(72) Inventors: Christof Merckle, Mannheim (DE); Erich Odermatt, Schaffhausen (CH)

(73) Assignee: Aesculap AG, Tuttlingen (DE)

( * ) Notice: Subject to any disclaimer, the term of this patent is extended or adjusted under 35 U.S.C. 154(b) by 766 days.

(21) Appl. No.: 14/765,592

(22) PCT Filed: Mar. 5, 2014

(86) PCT No.: PCT/EP2014/054219
§ 371 (c)(1),
(2) Date: Aug. 4, 2015

(87) PCT Pub. No.: WO2014/135566
PCT Pub. Date: Sep. 12, 2014

(65) Prior Publication Data
US 2015/0367042 A1 Dec. 24, 2015

(30) Foreign Application Priority Data
Mar. 8, 2013 (DE) .................. 10 2013 203 988

(51) Int. Cl.
*A61L 24/00* (2006.01)
*A61L 24/10* (2006.01)
*A61L 31/14* (2006.01)
*A61L 31/16* (2006.01)
*A61B 18/14* (2006.01)
*A61L 31/04* (2006.01)
*B05D 1/00* (2006.01)
*B05D 1/16* (2006.01)
*A61B 18/00* (2006.01)
*A61B 17/00* (2006.01)

(52) U.S. Cl.
CPC ............. *A61L 31/14* (2013.01); *A61B 18/14* (2013.01); *A61L 24/001* (2013.01); *A61L 24/0015* (2013.01); *A61L 24/0042* (2013.01); *A61L 24/102* (2013.01); *A61L 31/044* (2013.01); *A61L 31/148* (2013.01); *A61L 31/16* (2013.01); *B05D 1/007* (2013.01); *B05D 1/16* (2013.01); *A61B 2017/00004* (2013.01); *A61B 2018/0063* (2013.01)

(58) Field of Classification Search
CPC ........ A61L 31/044; A61L 31/14; A61L 31/16; A61L 24/001; A61L 24/0015; A61L 24/0042; A61L 24/102
See application file for complete search history.

(56) References Cited

U.S. PATENT DOCUMENTS

| | | |
|---|---|---|
| 3,896,802 A | 7/1975 | Williams |
| 2001/0056303 A1 | 12/2001 | Caneiro et al. |
| 2002/0037323 A1 | 3/2002 | Prasch et al. |

FOREIGN PATENT DOCUMENTS

| | | |
|---|---|---|
| CN | 102600013 | 3/2012 |
| DE | 10 2009 002 768 A1 | 11/2010 |
| EP | 0 134 813 A1 | 3/1985 |
| EP | 2 567 714 A1 | 3/2013 |
| WO | 84/03035 A1 | 8/1984 |
| WO | 00/24436 | 5/2000 |
| WO | 2008/125259 A2 | 10/2008 |
| WO | 2011/138347 A2 | 11/2011 |

OTHER PUBLICATIONS

First Office Action dated Jul. 22, 2016, of corresponding Chinese Application No. 201480013056.9 along with an English translation.
Second Office Action dated Mar. 13, 2017, of corresponding Chinese Application No. 201480013056.9 along with an English translation.

*Primary Examiner* — Zohreh A Fay
(74) *Attorney, Agent, or Firm* — Lewis Kohn & Walker LLP; David M. Kohn

(57) ABSTRACT

A tissue fusion agent includes a supporting element and a flock material. A surgical system includes the tissue fusion agent and a tissue fusion instrument. A method of producing the tissue fusion agent includes a) coating a supporting element with an adhesive, and b) flocking the adhesive-coated supporting element with a flock material while the adhesive is moist, adhesive or tacky, or after activation of the adhesive.

17 Claims, No Drawings

TISSUE FUSION AGENT

TECHNICAL FIELD

This disclosure relates to a tissue fusion agent, to a surgical system and to methods of producing the tissue fusion agent.

BACKGROUND

Tissue fusion (tissue connection), especially in the form of anastomoses and ligations (ligatures), can be carried out by various techniques, for example, suturing techniques and stapling techniques.

Newer tissue fusion techniques provide for the use of ultrasound, laser irradiation or heat. Although carrying out those techniques brings about tissue fusion which is reliable and safe from a medical point of view, the disadvantage is that part of the tissue in the fusion region always also becomes degenerated because of the energy input. In some circumstances, this can have an adverse effect on the strength and tightness of the fused tissue.

WO 2011/138347 A2 discloses a surgical system for electrosurgical tissue fusion comprising not only a surgical instrument having two high-frequency current electrodes (HF electrodes), but also a medically compatible material supporting the tissue connection. The material can be, in particular, a collagen disk.

The use of a biocompatible material layer as intermediate layer between body tissue surfaces to be fused is disclosed in DE 10 2009 002 768 A1.

A fundamental disadvantage of the known tissue fusion materials is the application thereof into a tissue region to be fused, the application being very complicated in some cases. A further difficulty is that of achieving a most uniform distribution of the materials in a tissue region to be fused. Moreover, a possible result of inhomogeneities with regard to the material thickness is that the material contracts with great variation upon input of energy. Hence, there is the risk of there being insufficient material provided for strong and tight tissue fusion. If gels and liquids are used to achieve tissue fusion, a disadvantage is that they can be displaced during the fusion process from the tissue region to be fused.

SUMMARY

We provide a tissue fusion agent including a supporting element and a flock material.

We also provide a surgical system including the tissue fusion agent including a supporting element and a flock material and a tissue fusion instrument, the instrument preferably including at least two electrodes for releasing or taking up current, more particularly high-frequency current (HF current).

We further provide a method of producing the tissue fusion agent including a supporting element and a flock material, including a) coating a supporting element with an adhesive, and b) flocking the adhesive-coated supporting element with a flock material while the adhesive is moist, adhesive or tacky, or after activation of the adhesive.

We further yet provide a method of producing the tissue fusion agent including a supporting element and a flock material, including a) at least partly transferring a supporting element to an adhesive or tacky state, and b) flocking the at least partly adhesive or tacky supporting element with a flock material.

DETAILED DESCRIPTION

We provide a tissue fusion agent, i.e., an agent for use in the fusion or connection or the closure of tissue, generally body tissue.

The tissue fusion agent comprises a supporting element and a flock material.

The tissue fusion agent has the following advantages:

Owing to the presence of the flock material, the tissue fusion agent has altogether an enlarged surface area, making it possible to establish improved contact with a tissue region to be fused, the contact being improved in terms of strength and tightness with regard to the fusion to be achieved.

In addition, the tissue fusion agent comprising the flock material provides additional material, thereby ensuring that sufficient material is provided, after application into a tissue region to be fused, for strong and, in particular, tight, compact and penetrative tissue fusion.

A further advantage associated with the surface area which is enlarged due to the flock material is that the supporting element can be thinner and thus more flexible, and nonetheless sufficient material is provided to achieve strong and, in particular, tight, compact and penetrative tissue fusion.

Another advantage is that the tissue fusion agent owing to its surface area which is enlarged (due to the presence of the flock material) can be applied into a tissue region to be fused in a more uniform and, in particular, more homogeneous manner compared to generic materials. As a result, any inhomogeneities in the thickness of the supporting element can be more effectively compensated for during the fusion process.

In addition, the enlarged surface area of the tissue fusion agent allows, with particular advantage, complete covering of a tissue region to be fused, without complicated adaptations of the tissue fusion agent to the proportions of the tissue region to be fused being required before or during the tissue fusion process.

Nevertheless, it may be advantageous to perform indication-specific adaptations, for example, in the form of punch-outs to match the tissue fusion agent and the body structures to be anastomized (for example, blood vessel sections, intestinal sections, lymphatic vessel sections or nerve pathway sections), more particularly the wall thickness thereof.

Through the specific selection of materials and/or additives for the supporting element and/or the flock material, it is additionally possible to specifically influence or adjust fusion properties of the tissue fusion agent such as, for example, melting ability, adhesiveness and/or conductive or impedance behavior and also resorption properties of the tissue fusion agent. This allows not only fusion process-specific but also indication-specific adaptation of the tissue fusion agent. As a result, it is possible, for example, to ensure resorption of the tissue fusion agent and thus complete growth of cells, extracellular matrix or tissue through the fused tissue region.

The aspects listed above contribute, with particular advantage, to shortening the fusion process and thus shortening possible energy input (if the newer tissue fusion techniques mentioned at the start are used). Hence, the tissue fusion agent altogether also allows the performance of fusion which is more gentle to tissue.

Compared to gels and liquids, the advantage of the tissue fusion agent is that the risk of dislocation during the fusion process is comparatively low.

Altogether, the tissue fusion agent makes it possible to carry out a simple, reproducible and, in particular, wound healing-beneficial tissue fusion process.

The expression "supporting element" means a substrate or support for the flock material. The term "flock material" means a material which can be applied to the supporting element or to a surface of the supporting element by a flocking technique, preferably with the use of an adhesive. Generally, the material is fibers of a defined fiber length (preferred fiber lengths will be mentioned below) which can be usually produced by trimming to length, more particularly cutting, or milling of single fibers (for example, extrusion fibers), more particularly so-called continuous fibers.

Preferably, the tissue fusion agent therefore further comprises an adhesive layer. The adhesive layer can, in principle, continuously coat the supporting element or the surface thereof, i.e., over the entire surface. However, it is preferred when the adhesive layer coats the supporting element or the surface of the supporting element only in part or on subareas.

We can, in particular, provide for the coating of opposite sides, more particularly opposite main surfaces, of the supporting element by the adhesive layer. The term "main surfaces" means the sides of the supporting element having the greatest surface area. The adhesive layer can have a thickness of 1 μm to 500 μm, more particularly 3 μm to 300 μm, preferably 5 μm to 100 μm.

The flock material preferably connects to the adhesive layer. More particularly, the flock material connects to the supporting element or to a surface of the supporting element via the adhesive layer. To this end, the flock material generally partly, more particularly only partly, penetrates the adhesive layer. However, the flock material preferably does not penetrate the supporting element.

The flock material can penetrate the adhesive layer over a length of 0.5% to 95%, more particularly 3% to 50%, preferably 5% to 20%, based on its total length.

The adhesive layer is preferably present as a nontextile layer or coating. For example, the adhesive layer can be formed as a coat or finish, film, gel, more particularly hydrogel, paste or the like. The adhesive layer may form a proportion of 0.1% by weight to 90% by weight, more particularly 0.5% by weight to 50% by weight, preferably 1% by weight to 25% by weight, based on the total weight of the tissue fusion agent.

It is useful for the adhesive layer to comprise a biocompatible material or to be formed from such a material. Preferably, the adhesive layer comprises a resorbable material or is formed from such a material.

The material described in the last two examples is preferably a polymer, more particularly a copolymer. The term "copolymer" means a polymer composed of at least two different monomer units. Thus, the term "copolymer" encompasses not only copolymers in the narrower sense, i.e., so-called bipolymers (polymers composed of two different monomer units), but also terpolymers, tetrapolymers and the like. The copolymer can additionally be selected from the group comprising random copolymer, alternating copolymer, block copolymer or segmented copolymer, graft copolymer and mixtures, more particularly blends, thereof.

Preferably, the adhesive layer comprises a resorbable material or is formed from a resorbable material which is selected from the group comprising polyhydroxyalkanoates, proteins, extracellular proteins, serum proteins, polysaccharides, mucopolysaccharides, carboxyl group-bearing polysaccharides, amino group-bearing polysaccharides, aldehyde group-bearing polysaccharides, copolymers thereof, salts thereof, stereoisomers, more particularly diastereomers, thereof and mixtures, more particularly blends, thereof.

More particularly, the adhesive layer can comprise a resorbable material or can be formed from a resorbable material which is selected from the group comprising polyglycolic acid or polyglycolide, polylactic acid or polylactide, polydioxanone, polytrimethylene carbonate, poly-ε-caprolactone, poly-3-hydroxybutyric acid or poly-3-hydroxybutyrate, poly-4-hydroxybutyric acid or poly-4-hydroxybutyrate, polysaccharides, cellulose, cellulose derivatives, alkylcelluloses, methylcellulose, hydroxyalkylcellulose, hydroxymethylcellulose, hydroxyethylcellulose, hydroxypropylcellulose, carboxyalkylcelluloses, carboxymethylcellulose, starch, amylose, amylopectin, dextran, dextrin, chitin, chitosan, hyaluronic acid, dextran sulfate, heparin, heparan sulfate, chondroitin sulfate, dermatan sulfate, collagen, gelatin, elastin, reticulin, fibronectin, laminin, fibrin, fibrinogen, albumin, copolymers thereof, salts thereof and mixtures, more particularly blends, thereof.

Alternatively, the flock material connects directly, i.e., with no adhesive layer, to the supporting element or to a surface of the supporting element. To this end, the flock material generally penetrates the supporting element. For example, the flock material can penetrate the supporting element over a length of 0.5% to 95%, more particularly 3% to 50%, preferably 5% to 20%, based on its total length.

The supporting element is preferably formed as a planar structure, more particularly a two- or three-dimensional planar structure. The supporting element can, in particular, be layered or in the form of a ply (ply of material), a film, sheet, membrane, disk or the like. Preferably, the supporting element is disk-shaped, more particularly in the form of an oval, preferably circular or ellipsoidal, disk or in the form of a noncircular disk, preferably in the form of a sheet. Particularly preferably, the supporting element is annular or substantially annular.

The supporting element can, in particular, be present in the form of a circular ring, the ring width of which corresponds to the wall thickness or substantially corresponds to the wall thickness of body structures to be anastomized, such as, in particular, blood vessel sections, intestinal sections, lymphatic vessel sections and/or nerve pathway sections.

To speed up resorption of the tissue fusion agent, it is possible in further examples for the supporting element to comprise holes, perforations, punch-outs or the like. Furthermore, the supporting element can have a thickness of 1 μm to 5 mm, more particularly 2 μm to 2 mm, preferably 20 μm to 1 mm.

The supporting element may be composed of two or more supporting element layers, preferably two supporting element layers. The supporting element layers can be connected, preferably adhesively bonded, to one another via unflocked sides, more particularly main surfaces. The flock material is preferably arranged on those sides which are opposite the sides of the supporting element layers that are connected to one another.

The supporting element may comprise a coagulative and/or hot-melt adhesive material or is formed from such a material. More particularly, the supporting element comprises a material which is meltable under the influence of high-frequency alternating current (HF current), heat, ultrasound and/or laser irradiation or is formed from such a material. Preferably, the supporting element comprises a material which is meltable under the influence of an alternating current having a frequency of 200 kHz to 4000 kHz, more particularly 100 kHz to 600 kHz, preferably 250 kHz to 500 kHz, or is formed from such a material.

Particularly preferably, the supporting element comprises a resorbable material or is formed from such a material. This ensures that cells, extracellular matrix or tissue grow through the supporting element, making it possible to achieve an increase in strength of fusion (compared to tissue fusion without use of the tissue fusion agent). The material described in the preceding examples for the supporting element can, in a further example, be of synthetic, biological and/or recombinant origin.

As an alternative or in addition, the material for the supporting element can be of natural or native origin. The material can, in particular, be of xenogeneic origin, preferably porcine, bovine and/or equine origin. Alternatively, the material for the supporting element can also be of human origin.

Preferably, the material for the supporting element is a polymer, more particularly one selected from the group comprising synthetic polymer, recombinant polymer, naturally occurring polymer or biopolymer and mixtures, more particularly blends, thereof.

Preferably, the supporting element comprises a resorbable material or is formed from such a material which is selected from the group comprising polyhydroxyalkanoates, proteins, extracellular proteins, serum proteins, polysaccharides, mucopolysaccharides, carboxyl group-bearing polysaccharides, amino group-bearing polysaccharides, aldehyde group-bearing polysaccharides, copolymers thereof, salts thereof, stereoisomers, more particularly diastereomers, thereof and mixtures, more particularly blends, thereof.

More particularly, the supporting element can comprise a resorbable material or can be formed from such a material which is selected from the group comprising polyglycolide or polyglycolic acid, polylactide or polylactic acid, polydioxanone, poly-3-hydroxybutyrate or poly-3-hydroxybutyric acid, poly-4-hydroxybutyrate or poly-4-hydroxybutyric acid, polytrimethylene carbonate, poly-ε-caprolactone, polyvinyl alcohol, cotton, cellulose, cellulose derivatives such as, for example, alkylcelluloses, methylcellulose, hydroxyalkylcelluloses, hydroxymethylcellulose, hydroxyethylcellulose, hydroxypropylcellulose, carboxyalkylcelluloses, carboxymethylcellulose, starch, amylose, amylopectin, dextran, dextrin, chitin, chitosan, hyaluronic acid, dextran sulfate, heparin, heparan sulfate, chondroitin sulfate, dermatan sulfate, collagen, gelatin, elastin, reticulin, fibronectin, laminin, fibrin, fibrinogen, albumin, copolymers thereof, salts thereof, stereoisomers, more particularly diastereomers, thereof and mixtures, more particularly blends, thereof.

The supporting element may comprise a polyethylene glycol or is formed from a polyethylene glycol. The supporting element can comprise a material having a melting point below 100° C., in particular having a melting point 70° C. to 90° C., or can be formed of such a material.

The flock material can be a particulate and/or fibrous flock material or can be flock fibers. The particulate and/or fibrous flock material can be present in milled form. More particularly, the particulate and/or fibrous flock material can be milled fibers, more particularly milled flock fibers.

The particulate flock material can be present in the form of a powder or granules. For example, the particulate flock material can have a particle size or particle diameter of 0.05 µm to 5 mm, more particularly 0.1 µm to 3 mm, preferably 10 µm to 2 mm. Particularly preferably, the fibrous flock material is present in the form of flock fibers, more particularly monofilament flock fibers.

The fibrous flock material can additionally be textured and/or nontextured.

Preferably, the fibrous flock material has a uniform and defined fiber length. The fibrous flock material can, in principle, have a fiber length of 40 µm to 15 mm, more particularly 50 µm to 10 mm, preferably 100 µm to 5.0 mm. More particularly, the fibrous flock material can have a fiber length of 10 µm to 5 mm, more particularly 40 µm to 4 mm, preferably 50 µm to 3 mm, more preferably 100 µm to 2 mm. Particularly preferably, the fibrous flock material can have a fiber length of 100 µm to 3 mm, preferably 200 µm to 2 mm.

Furthermore, the fibrous flock material can have a fiber thickness or fiber diameter of 5 µm to 800 µm, more particularly 7 µm to 300 µm, preferably 10 µm to 150 µm.

In addition, the fibrous flock material can have a linear density of 0.01 dtex to 1000 dtex, more particularly 0.1 dtex to 500 dtex, preferably 0.3 dtex to 200 dtex. The fibrous flock material can, in particular, have a linear density of 0.1 dtex to 50 dtex, preferably 0.9 dtex to 22 dtex, more preferably 1 dtex to 10 dtex. The dimension "dtex" (decitex) means a linear density of 1 g per 10 000 m length of the fibrous flock material.

The flock material can protrude over a length of 10 µm to 5 mm, more particularly 40 µm to 4 mm, preferably 50 µm to 3 mm, from the supporting element or from a surface of the supporting element or an adhesive layer covering the surface of the supporting element.

The flock material can be arranged on two opposite sides, more particularly on two opposite main surfaces, of the supporting element or protrude from two opposite sides, more particularly two opposite main surfaces, of the supporting element.

The flock material can be arranged perpendicular or substantially perpendicular to the supporting element or to a surface of the supporting element. The term "substantially perpendicular" can include deviations from the right angle of up to 5°.

Alternatively, the flock material may be arranged at an oblique angle with respect to the supporting element or to a surface of the supporting element, the oblique angle being greater than 0°, but smaller than 85°.

The flock material can be arranged at a density of 1% to 30%, more particularly 5% to 25%, preferably 10% to 20%, on the supporting element or on a surface of the supporting element. The flock material may be arranged on the supporting element or on a surface of the supporting element in the form of particles and/or fibers at a density of 1 to 2000 particles and/or fibers per mm$^2$, more particularly 5 to 1000 particles and/or fibers per mm$^2$, preferably 10 to 500 particles and/or fibers per mm$^2$.

In addition, the flock material can be arranged on the supporting element or on a surface of the supporting element in the form of a pattern or in an irregular or randomized manner. For example, the flock material can be arranged on the supporting element or on a surface of the supporting element in the form of a linear arrangement, graduated arrangement, helical or spiral arrangement, meandering arrangement, serpentine arrangement, sinusoidal arrangement, annular arrangement and combinations thereof.

It may be further preferable for the flock material to be arranged on the supporting element or on a surface of the supporting element in a pattern which, for example, corresponds to the cross section of body structures to be anastomized such as, for example, blood vessel sections, intestinal sections, lymphatic vessel sections, nerve pathway sections or the like. Accordingly, it may be preferable for the flock material to be arranged on the surface of the supporting element in an oval, more particularly circular, preferably annular, pattern or in an ellipsoidal pattern.

Furthermore, the fibrous flock material can have a circular cross section or a non-circular cross section, more particularly an oval, ellipsoidal, polygonal, for example, triangular, rectangular, square, rhomboidal, pentagonal, hexagonal and/or star-shaped, cross section.

Furthermore, the tissue fusion agent can have a flock material content of 0.01% by weight to 50% by weight, more particularly 0.5% by weight to 20% by weight, preferably 1.0% by weight to 10% by weight, based on the total weight of the tissue fusion agent.

The flock material may comprise a coagulative and/or hot-melt adhesive material or is formed from such a material. More particularly, the flock material comprises a material which is meltable under the influence of high-frequency alternating current (HF current), heat, ultrasound and/or laser irradiation or is formed from such a material. Preferably, the flock material comprises a material which is meltable under the influence of an alternating current having a frequency of 200 kHz to 4000 kHz, more particularly 100 kHz to 600 kHz, preferably 250 kHz to 500 kHz, or is formed from such a material.

Particularly preferably, the flock material comprises a resorbable material or is formed from such a material.

The material described in the preceding examples for the flock material can, in a further example, be of synthetic, biological and/or recombinant origin.

As an alternative or in addition, the material for the flock material can be of natural or native origin. The material can, in particular, be of xenogeneic origin, preferably porcine, bovine and/or equine origin. As an alternative or in addition, the material for the flock material can be of human origin. In these examples, the flock material is preferably present as milled flock material.

Preferably, the material for the flock material is a polymer, more particularly a copolymer. The polymer can, in particular, be selected from the group comprising synthetic polymer, recombinant polymer, naturally occurring polymer or biopolymer, copolymers thereof and mixtures, more particularly blends, thereof.

Preferably, the flock material comprises a resorbable material or is formed from such a material which is selected from the group comprising polyhydroxyalkanoates, proteins, extracellular proteins, serum proteins, polysaccharides, mucopolysaccharides, carboxyl group-bearing polysaccharides, amino group-bearing polysaccharides, aldehyde group-bearing polysaccharides, copolymers thereof, salts thereof, stereoisomers, more particularly diastereomers, thereof and mixtures, more particularly blends, thereof.

More particularly, the flock material can comprise a resorbable material or can be formed from such a material which is selected from the group comprising polyglycolide or polyglycolic acid, polylactide or polylactic acid, polydioxanone, poly-3-hydroxybutyrate or poly-3-hydroxybutyric acid, poly-4-hydroxybutyrate or poly-4-hydroxybutyric acid, polytrimethylene carbonate, poly-ε-caprolactone, polyvinyl alcohol, cotton, cellulose, cellulose derivatives such as, for example, alkylcelluloses, methylcellulose, hydroxyalkylcelluloses, hydroxymethylcellulose, hydroxyethylcellulose, hydroxypropylcellulose, carboxyalkylcelluloses, carboxymethylcellulose, starch, amylose, amylopectin, dextran, dextrin, chitin, chitosan, hyaluronic acid, dextran sulfate, heparin, heparan sulfate, chondroitin sulfate, dermatan sulfate, collagen, gelatin, elastin, reticulin, fibronectin, laminin, fibrin, fibrinogen, albumin, copolymers thereof, salts thereof, stereoisomers, more particularly diastereomers, thereof and mixtures, more particularly blends, thereof.

The flock material may comprise a polyethylene glycol or is formed from a polyethylene glycol.

The flock material can comprise a material having a melting point below 100° C., in particular having a melting point 70° C. to 90° C., or can be formed of such a material.

It may be further preferable for the flock material to be present in the form of a mixture composed of different flock materials. In this case, the flock materials can differ from one another with regard to a parameter selected from the group comprising particle size (in a particulate flock material), fiber length (in a fibrous flock material), thickness or diameter, linear density (in a fibrous flock material) and/or materials. With regard to the parameters referred to in this paragraph, full reference is made to the description above.

The supporting element and the flock material can comprise the same material or can be formed from the same material. Alternatively, the supporting element and the flock material can comprise different materials or can be formed from different materials. With regard to the possible material(s), full reference is made to the description above.

Advantageously, the tissue fusion agent, more particularly the supporting element and/or the flock material, can be additized, i.e., comprise one or optionally more additives.

To achieve an increase in conductivity or decrease in impedance, it can be provided that the tissue fusion agent, more particularly the supporting element and/or the flock material, comprises a conductivity-increasing or impedance-decreasing additive, preferably in the form of a salt.

The conductivity-increasing or impedance-decreasing additive is preferably selected from the group comprising alkali metal halide, alkaline earth metal halide, phosphate, alkali metal phosphate, alkaline earth metal phosphate, mixed phosphates thereof and mixtures thereof.

For example, the conductivity-increasing or impedance-decreasing additive can be selected from the group comprising sodium chloride, potassium chloride, barium chloride, magnesium chloride, calcium chloride, sodium phosphate, potassium phosphate, barium phosphate, magnesium phosphate, calcium phosphate, mixed phosphates thereof and mixtures thereof.

The conductivity-increasing or impedance-decreasing additive can comprise a proportion of 0.1% by weight to 20% by weight, more particularly 0.1% by weight to 10% by weight, preferably 0.8% by weight to 5% by weight, based on the total weight of the tissue fusion agent, more particularly of the supporting sheet and/or of the flock material.

Alternatively, the flock material comprises a conductivity-decreasing additive, preferably in the form of a metal, for example, selected from the group comprising aluminum, iron, silver, zinc, magnesium and mixtures, more particularly alloys, thereof.

To achieve a biological, pharmaceutical and/or medical effect, it can be provided in an alternative or additional example that the tissue fusion agent, more particularly the supporting element and/or the flock material, comprises an active ingredient selected from the group comprising biological active ingredient, pharmaceutical active ingredient, medical active ingredient and mixtures thereof.

The tissue fusion agent, more particularly the supporting element and/or the flock material, can comprise an active ingredient selected from the group comprising antimicrobial, more particularly antibiotic, active ingredient, wound healing-promoting active ingredient, disinfecting active ingredient, anti-inflammatory active ingredient, blood coagulation-promoting active ingredient, growth factors, cell-differentiating factors, cell-adhesive factors, cell-recruiting factors, cell receptors, cell-binding factors, cytokines, peptides, structural proteins, extracellular proteins such as, for example, collagen, serum proteins such as, for example, albumin, polysaccharides such as, for example, hyaluronic acid, oligonucleotides, polynucleotides, DNA, RNA, salts thereof, stereoisomers, more particularly diastereomers, thereof and mixtures thereof.

For example, the tissue fusion agent, more particularly the supporting element and/or the flock material, can comprise an active ingredient selected from the group comprising biguanides, polyhexamethylene biguanide (PHMB), triclosan, chlorhexidine, gentamicin, vitamins, copper, zinc, silver, gold, salts thereof, stereoisomers, more particularly diastereomers, and mixtures thereof.

To increase the stability of the tissue fusion agent, more particularly the supporting element and/or the flock material, we can provide in a further example that the tissue fusion agent, more particularly the supporting element and/or the flock material, is present in crosslinked form. The tissue fusion agent, more particularly the supporting element and/or the flock material, can be physically and/or chemically crosslinked. Physical crosslinking of the tissue fusion agent, more particularly the supporting element and/or the flock material, can be achieved, for example, by appropriate irradiation techniques. Chemical crosslinking can generally be realized by appropriate chemical crosslinkers.

For example, the tissue fusion agent, more particularly the supporting element and/or the flock material, can be crosslinked using a chemical crosslinker selected from the group comprising aldehydes such as, for example, formaldehyde, dialdehydes such as, for example, glutaraldehyde, polyaldehydes such as, for example, dextran aldehyde, carbodiimides, diisocyanates such as, for example, hexamethylene diisocyanate, salts thereof and mixtures thereof.

The tissue fusion agent can be present in the form of the supporting element and the flock material or consist of the supporting element and the flock material, it optionally being possible for the supporting element and/or the flock material to be additized. With regard to further features and advantages of the supporting element and the flock material, full reference is made to the description above.

The tissue fusion agent is preferably a surgical tissue fusion agent. The tissue fusion agent is generally suited to closing, occluding or sealing biological tissue, more particularly human and/or animal tissue. Thus, the tissue fusion agent can in particular act as an occlusion agent.

Particularly preferably, the tissue fusion agent is used for carrying out anastomoses and/or ligations. The anastomoses can, in particular, be end-to-end anastomoses, side-to-end anastomoses, end-to-side anastomoses and side-to-side anastomoses. Furthermore, the anastomoses can be selected from the group comprising vascular anastomoses, more particularly blood vessel and/or lymphatic vessel anastomoses, intestinal anastomoses, and nerve anastomoses.

Furthermore, the tissue fusion agent can be used for tissue closure or for tissue sealing, especially after resections, preferably after partial resections, for example, in the case of organs.

A further preferred area of application concerns the use of the tissue fusion agent in carrying out electrosurgical fusion of body tissue.

The tissue fusion agent may be present in sterile and, in particular, off-the-shelf form. Sterilization of the tissue fusion agent can, for example, be achieved using ethylene oxide.

We provide a surgical system comprising the tissue fusion agent and a tissue fusion instrument. The tissue fusion instrument preferably comprises at least two electrodes that release or take up current, more particularly high-frequency current (HF current). Alternatively, the tissue fusion instrument can be a laser instrument or an instrument that generates ultrasonic waves.

However, the surgical system is preferably an electrosurgical system comprising the tissue fusion agent and at least two electrodes for releasing or taking up current, more particularly high-frequency current (HF current). Preferably, the two electrodes are component of a surgical instrument having two tool elements which are movable relative to one another and which each comprise one of the two electrodes, which, preferably in a convergence position of the tool elements, define a minimum distance from one another, lie opposite one another and face one another. With regard to such a surgical instrument, reference is made to WO 2011/138347 A2, the full disclosure of which is incorporated herein by reference.

With regard to further features and advantages of the surgical system, especially the tissue fusion agent, the supporting element and/or the flock material, full reference is made to the description above.

We further provide a method of producing a tissue fusion agent, more particularly the tissue fusion agent described above, the method comprising the following steps:
 a) coating a supporting element with an adhesive, and
 b) flocking the adhesive-coated supporting element with a flock material while the adhesive is moist, adhesive or tacky, or after activation of the adhesive.

The term "flocking" means a technique of applying the flock material, especially in the form of fibers, to the supporting element or to the adhesive layer (at least partly) coating the supporting element or a surface of the supporting element.

The term "activation" or "activate" shall include a technique which makes it possible to render the adhesive moist, adhesive or tacky. Corresponding techniques can be selected from the group comprising melting, liquification, moistening, soaking, dipping, heating, irradiation, ultrasonic wave generation, chemical usage and combinations thereof.

Coating the supporting element or of a surface thereof with the adhesive can, for example, be performed by extrusion, injection, casting, screen printing, dipping, soaking, spraying, spreading, knife coating and/or rolling techniques. The coating techniques described above are, in particular, dependent on the adhesive specifically used.

If the adhesive comprises, for example, a meltable material or the adhesive is formed from such a material, the adhesive can be applied to the supporting element or to a surface thereof by an extrusion technique.

By contrast, if the adhesive is present as an aqueous liquid, more particularly an aqueous solution, it may be preferable to apply the adhesive to the supporting element or to a surface thereof by a dipping, spraying or spreading technique. If the adhesive is present as a paste or gel, more particularly a hydrogel, it may be advantageous to apply the adhesive to the supporting element or to a surface thereof by brushing, spreading, knife coating, rolling or the like.

The supporting element or a surface thereof can, in principle, be flocked by scattering techniques, spraying techniques, blowing techniques, vibration techniques and/or electrostatic techniques. Preferably, the supporting element or a surface thereof is flocked by electrostatic flocking. In the case of electrostatic flocking, the flock material is applied in an electric field to the supporting element or to the adhesive layer coating the supporting element or a surface thereof.

The electrostatic flocking is carried out in a flocking apparatus. The flocking apparatus generally receives a negative charge, whereas the supporting element is generally grounded. As a result, the flock material usually "shoots" in a perpendicular or substantially perpendicular manner to the supporting element or to the adhesive layer coating the supporting element or a surface thereof.

Owing to the high acceleration experienced by the flock material in the electric field, good penetration of the flock material into the supporting element or into the adhesive layer is generally achieved.

Preferably, the supporting element is used as an electrode, more particularly a grounded electrode, together with a counter electrode, more particularly a high-voltage electrode. Particularly preferably, the supporting element is used as a cathode and the counter electrode, preferably a high-voltage electrode, is used as an anode.

The distance between the electrodes (supporting element and counter electrode) can be 2 cm to 200 cm, more particularly 5 cm to 100 cm, preferably 7 cm to 50 cm.

Furthermore, to carry out electrostatic flocking, a voltage of 5 kV (kilovolt) to 120 kV (kilovolt), more particularly 10 kV (kilovolt) to 100 kV (kilovolt), preferably 20 kV (kilovolt) to 80 kV (kilovolt), can be applied between the electrodes.

With regard to further features and advantages of the method described in the preceding examples, especially the tissue fusion agent, the supporting element and/or the flock material, full reference is made to the description above.

We further provide an alternative method of producing a tissue fusion agent, more particularly the tissue fusion agent described above. The method comprises the following steps:

a) at least partly transferring a supporting element to an adhesive or tacky state, and b) flocking the at least partly adhesive or tacky supporting element with a flock material.

For example, the supporting element can be transferred to an at least partly adhesive or tacky state by melting, liquification, moistening, soaking, dipping, heating, irradiation, ultrasonic wave generation, chemical usage or combinations thereof.

The supporting element is only partly transferred to an adhesive or tacky state. Preferably, one or more surface layers of the supporting element are transferred to an adhesive or tacky state.

With regard to further features and advantages of the method, especially the tissue fusion agent, the supporting element and/or the flock material, full reference is similarly made to the description above.

Further features and advantages are revealed by the following description of preferred examples. Individual features can, in each case, be realized on their own or in combination with one another. The preferred examples serve solely to further elucidate agents, systems and methods and to provide a better understanding, without restricting the disclosure thereto.

EXAMPLES

1. Production of Flock Fibers

Using an extrusion apparatus, fibers composed of collagen were extruded and subsequently trimmed to lengths of 100 µm to form flock fibers.

2. Flocking a Supporting Sheet Composed of Polyglycolide

A supporting sheet composed of polyglycolide and coated with a still moist or adhesive adhesive layer was flocked in a flocking cabin with the collagen flock fibers produced in step 1 by application of a high voltage of 60 kV to one of its two main surfaces.

After the adhesive layer was cured, the opposite main surface of the supporting sheet was flocked with the collagen flock fibers in a corresponding manner.

Subsequently, the tissue fusion agent thus obtained was packed, and sterilized using ethylene oxide.

3. Flocking a Polyglycolide Supporting Element Composed of Two Supporting Sheets A supporting sheet composed of polyglycolide and coated with a still moist or adhesive adhesive layer was flocked in a flocking cabin with the collagen flock fibers produced in step 1 by application of a high voltage of 60 kV to one of its two main surfaces.

Subsequently, a second supporting sheet likewise consisting of polyglycolide and having a likewise still moist or adhesive adhesive layer was flocked with the collagen flock fibers in a corresponding manner.

Thereafter, the two supporting sheets were adhesively bonded to one another along their unflocked main surfaces.

Subsequently, the tissue fusion agent thus obtained was packed, and sterilized using ethylene oxide.

4. Flocking a Supporting Film Composed of poly(ε-caprolactone-co-trimethylene carbonate)

Using an extrusion apparatus, fibers composed of poly(ε-caprolactone-co-trimethylene carbonate) were produced and subsequently trimmed to flock fibers of 100 µm in length using a precision cutting device.

The flock fibers were subsequently saturated in a calcium chloride-containing water bath with the conductivity-increasing salt.

After removal from the water bath and subsequent drying, the flock fibers were applied to the two main surfaces of a film composed of poly(ε-caprolactone-co-trimethylene carbonate) and having a thickness of 200 µm by application of an electric field. The adhesive used to connect the flock fibers to the supporting film was the film surface melted by infrared radiation.

From the supporting film thus flocked, annular pieces were subsequently punched out, the ring width of which corresponded to the wall thicknesses of different intestinal sections.

5. Flocking a Supporting Film Composed of Polyvinyl Alcohol

A supporting film composed of polyvinyl alcohol and having a thickness of 200 µm was flocked with flock fibers composed of albumin (fiber length 100 µm) on both of its main surfaces.

The adhesive used was the film surface rendered tacky by sprayed-on water.

After the flocking operation, the flocked supporting film thus obtained was dried.

6. Carrying Out Anastomosis of the Small Intestine

Resection was carried out in a small intestine in an animal (pig). Subsequently, the resulting ends of the small intestine were brought parallel to one another and, via two incisions, a two-armed HF instrument was introduced into the intestine.

While the two instrument arms were brought together, a tissue fusion agent in the form of a supporting sheet consisting of polyglycolide and flocked on one side with collagen fibers of 5 mm in length was introduced into the fusion site. The collagen fibers pointed inward into the fusion site.

While the tissue fusion was carried out, the collagen fibers melted and joined to the tissue. The supporting sheet likewise melted and brought about additional sealing of the fusion exterior (in the manner of "clotting").

Finally, a cut was made between the anastomosis, producing in turn a continuous lumen in the tissue fusion region. After closure of the incisions (by suturing or renewed fusion), the operation was ended.

The invention claimed is:

1. A tissue fusion agent comprising a supporting element and a flock material, wherein the supporting element comprises a material which is meltable under the influence of high-frequency alternating current, heat, ultrasound and/or laser irradiation or is formed from such a material, and wherein the flock material connects directly to a surface of the supporting element with no adhesive layer in between the flock material and the surface of the supporting element.

2. The tissue fusion agent according to claim 1, wherein the supporting element is formed as a two-dimensional planar structure in the form of a disk.

3. The tissue fusion agent according to claim 1, wherein the supporting element is in the form of a sheet.

4. The tissue fusion agent according to claim 1, wherein the supporting element is in the form of an annular disk.

5. The tissue fusion agent according to claim 1, wherein the flock material is in the form of monofilament flock fibers.

6. The tissue fusion agent according to claim 1, wherein the flock material is in the form of a particulate flock material.

7. The tissue fusion agent according to claim 1, wherein the supporting element and/or the flock material comprises a resorbable material or is formed from such a material which is preferably selected from the group comprising polyhydroxyalkanoates, polyvinyl alcohol, proteins, extracellular proteins, serum proteins, polysaccharides, mucopolysaccharides, carboxyl group-bearing polysaccharides, amino group-bearing polysaccharides, aldehyde group-bearing polysaccharides, copolymers thereof, salts thereof, stereoisomers, diastereomers thereof, mixtures, and blends thereof.

8. The tissue fusion agent according to claim 1, wherein the supporting element and/or the flock material comprises a conductivity-increasing or impedance-decreasing additive in the form of a salt.

9. The tissue fusion agent according to claim 8, wherein the conductivity-increasing or impedance-decreasing additive is selected from the group consisting of alkali metal halide, alkaline earth metal halide, phosphate, alkali metal phosphate, alkaline earth metal phosphate, mixed phosphates and mixtures thereof.

10. The tissue fusion agent according to claim 1, wherein the supporting element and/or the flock material comprises a conductivity-decreasing additive in the form of a metal.

11. The tissue fusion agent according to claim 1, wherein the supporting element and/or the flock material comprises an active ingredient selected from the group consisting of biological active ingredient, pharmaceutical active ingredient, medical active ingredient and mixtures thereof.

12. The tissue fusion agent according to claim 1 as surgical tissue fusion agent for use in carrying out anastomoses and/or ligations and/or for tissue closure after resections or partial resections in organs.

13. The tissue fusion agent according to claim 1 for use in the electrosurgical fusion of body tissue.

14. A surgical system comprising a tissue fusion agent according to claim 1 and a tissue fusion instrument, the instrument preferably comprising at least two electrodes for releasing or taking up current, more particularly high-frequency current (HF current).

15. A method of producing a tissue fusion agent according to claim 1, comprising:
 a) coating a supporting element with an adhesive, and
 b) flocking the adhesive-coated supporting element with a flock material while the adhesive is moist, adhesive or tacky, or after activation of the adhesive.

16. A method of producing a tissue fusion agent according to claim 1, comprising:
 a) at least partly transferring a supporting element to an adhesive or tacky state, and
 b) flocking the at least partly adhesive or tacky supporting element with a flock material.

17. A tissue fusion agent comprising a supporting element and a flock material, wherein the supporting element comprises a material which is meltable under the influence of high-frequency alternating current, heat, ultrasound and/or laser irradiation or is formed from such a material, and wherein the flock material is arranged perpendicular or substantially perpendicular to a surface of the supporting element.

* * * * *